(12) United States Patent
Van Nguyen et al.

(10) Patent No.: US 6,458,155 B1
(45) Date of Patent: Oct. 1, 2002

(54) FRESH DONOR HEART VALVE SIZER AND METHOD OF USE

(75) Inventors: Son Van Nguyen, Irvine; Hung Lam, Norco; Cuong Ton-That, Irvine, all of CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 30 days.

(21) Appl. No.: 09/653,799

(22) Filed: Sep. 1, 2000

(51) Int. Cl.[7] .................................................. A61F 2/06
(52) U.S. Cl. ...................... 623/2.11; 623/901; 623/909; 623/913; 33/511
(58) Field of Search .............................. 623/2.11, 66.1, 623/901, 902, 904, 909, 910, 913; 33/511, 512, 513, 514.1, 514.2, 515; 128/898, 887; 606/144

(56) References Cited

U.S. PATENT DOCUMENTS

| | | | |
|---|---|---|---|
| 4,211,241 A | * 7/1980 | Kaster et al. | 128/774 |
| 4,372,743 A | 2/1983 | Lane | |
| 5,011,481 A | 4/1991 | Meyers et al. | |
| 5,042,161 A | 8/1991 | Hodge | |
| 5,197,979 A | 3/1993 | Quintero et al. | |
| 5,814,098 A | * 9/1998 | Hinnenkamp et al. | 623/2 |
| 5,961,539 A | 10/1999 | Northrup, III et al. | |
| 6,001,126 A | 12/1999 | Nguyen-Thien-Nhon | |
| 6,166,184 A | * 12/2000 | Hendriks et al. | 530/356 |
| 6,214,054 B1 | * 4/2001 | Cunanan et al. | 623/23.72 |

FOREIGN PATENT DOCUMENTS

EP       0 584489 A1    3/1994
WO       WO99/11200 A1  3/1999

OTHER PUBLICATIONS

Study "Longitudinal and Radial Distensibility of the Porcine Aortic Root" by Bjarne Hansen Department of Electrical Engineering, University of Western Ontario, London, Ontario, Jun. 1994.

* cited by examiner

*Primary Examiner*—David J. Isabella
*Assistant Examiner*—Urmi Chattopadhyay
(74) *Attorney, Agent, or Firm*—Debra D. Condino; John Christopher James; Guy L. Cumberbatch (57) ABSTRACT

A donor heart valve sizer and method of sizing to increase the quality and yield of, and decrease the expense of fabricating, prosthetic heart valves. The sizer includes an axially-extending sizing portion sized to fit within the lumen of a donor heart valve. The sizing portion may be conical such that a resistance to further insertion is felt when the exterior of the sizing portion contacts the annulus of the valve. A measuring bracket attached to the sizing portion includes a scale aligned with the sizing portion that indicates the final expected valve size based on the position of the fresh donor valve on the sizing portion. The measuring bracket includes regions of acceptable valve sizes, and may also include regions of unacceptable valve sizes. A method of sizing includes utilizing the sizer in the slaughterhouse to reduce the overall number of valves shipped to the valve assembly facility to obtain a particular valve size. The sizer and method are particular useful for sizing xenograft valves, especially porcine aortic valves. The sizing portion may be made of polytetrafluoroethylene, and have an included taper of approximately 4°.

37 Claims, 5 Drawing Sheets

| | 21 | 23 | 25M | 25A | 27M | 27A | 29M | 29A | 31 | 33 | 35 |
|---|---|---|---|---|---|---|---|---|---|---|---|
| MO. 1 | 1.7% | 17.9% | 34.1% | 30.4% | 9.1% | 6.8% | 0.0% | 0.0% | 0.0% | 0.0% | 0.0% |
| MO. 2 | 0.0% | 50.0% | 17.7% | 34.4% | 37.2% | 6.5% | 3.3% | 0.5% | 0.0% | 0.0% | 0.0% |
| MO. 3 | 0.0% | 1.2% | 25.1% | 41.5% | 26.9% | 1.8% | 3.5% | 0.0% | 0.0% | 0.0% | 0.0% |
| MO. 4 | 0.0% | 0.9% | 50.0% | 32.7% | 15.9% | 0.0% | 0.0% | 0.0% | 0.0% | 0.0% | 0.0% |
| SA 1 | 0.0% | 0.0% | 83.0% | 17.0% | 0.0% | 0.0% | 0.0% | 0.0% | 0.0% | 0.0% | 0.0% |
| SA 2 | 0.0% | 0.0% | 88.0% | 12.0% | 0.0% | 0.0% | 0.0% | 0.0% | 0.0% | 0.0% | 0.0% |
| SA 3 | 0.0% | 0.0% | 77.7% | 22.2% | 0.0% | 0.0% | 0.0% | 0.0% | 0.0% | 0.0% | 0.0% |
| SA 4 | 0.0% | 0.0% | 100.0% | 0.0% | 0.0% | 0.0% | 0.0% | 0.0% | 0.0% | 0.0% | 0.0% |
| SIZER 25A | 0.0% | 0.0% | 23.1% | 77.9% | 0.0% | 0.0% | 0.0% | 0.0% | 0.0% | 0.0% | 0.0% |

FIG. 7

FRESH DONOR HEART VALVE SIZER AND METHOD OF USE

FIELD OF THE INVENTION

The present invention pertains to an apparatus and method for manufacturing bioprosthetic heart valves and, more particularly, to a sizer and method of sizing fresh donor heart valves to facilitate the fabrication of bioprosthetic heart valves.

BACKGROUND OF THE INVENTION

Prosthetic heart valves are used to replace damaged or diseased heart valves. In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary valves. Prosthetic heart valves can be used to replace any of these naturally occurring valves, although repair or replacement of the aortic or mitral valves is most common because they reside in the left side of the heart where pressures are the greatest.

Where replacement of a heart valve is indicated, the dysfunctional valve is typically cut out and replaced with either a mechanical valve, or a tissue valve. Tissue (e.g., xenograft) valves are often preferred over mechanical valves because they typically do not require long-term treatment with anticoagulants. Although so-called stentless valves are available, the most widely used tissue valves include some form of stent or synthetic leaflet support. The most common tissue valves are constructed with an intact, multi-leaflet donor valve, or with separate leaflets cut from bovine (cow) pericardium, for example. The most common intact valve used for stented and stentless valves is the porcine (pig) aortic valve, although other porcine valves and valves from other animals (e.g., equine or marsupial donors) have been used. The present invention is not limited to the preparation of porcine valves, though existing bioprosthetic heart valves on the market are nearly exclusively made from porcine valves, and thus the description herein will focus on such valves.

In a typical prosthetic valve fabrication process, the fresh porcine heart is first harvested in a certified slaughterhouse from the animal, weighed, and sorted into various valve size ranges by means of either estimating sized by eye based on the flattened aortic width, or by heart weight to valve size correlation. Of course, this correlation is a very rough estimate, with actual valve sizes differing quite a bit within similarly-sized porcine hearts. The aortic valve and surrounding tissue (hereinafter termed the "aortic valve isolation") is then severed from the porcine heart. Because of its proximity to the aortic valve, the pulmonary artery remains connected to the aortic valve isolation. A cross-section of the aortic valve isolation can be seen in FIG. 4 in the context of the sizer and method of sizing of the present invention.

At this stage, a large number of aortic valve isolations are packed in ice and shipped from the slaughterhouse to the prosthetic valve manufacturing facility. At the manufacturing facility, the aortic valve isolation is further sorted by valve size by technicians trained to estimate such valve size using their fingers. That is, the orifice diameter of the aortic valve annulus is estimated by insertion of one or more fingers through the inflow end of the aortic valve isolation. Because of the rough nature of the heart weight to valve size estimation, a large proportion of valves are rejected at this stage, resulting in wasted inventory and shipping costs.

It should be noted that the aortic valve annulus defines the narrowest opening through the valve, and is the reference dimension for implantation purposes. That is, the annulus diameter of the human patient is measured using conventional surgical sizers to determine the orifice size of the replacement bioprosthetic valve. Conventional sizers for measuring the human valve annulus typically comprise a series of incrementally-sized cylindrical elements marked with the corresponding outside diameter in mm. Most sizer sets include cylindrical elements that range from a low of 19 mm to a high of 33 mm, in 2 mm increments, and a common handle for manipulating the sizers. Some sizers for measuring the human valve annulus are shaped, or include flanges or other stepped features to also provide a measurement of the aortic root adjacent to the annulus. The aortic root is that part of the valve anatomy between the annulus and the convex sinuses of the ascending aorta, and has a generally scalloped appearance with the valve leaflets being attached along alternating arcuate cusps and upstanding commissures around its border. In any event, the primary measurement derived from conventional surgical sizers is the annulus diameter determined by finding which sizer fits properly in the annulus based on tactile feedback.

Following the estimation of the porcine aortic valve annulus diameter by the finger measurement technique, the fresh valve is then trimmed and chemically fixed to render it biologically inert for implantation purposes. The trimming procedure typically involves cutting away the pulmonary artery and surrounding muscle tissue from the inflow end of the valve. What is left is a generally tubular valve element having a small amount of tissue on the inflow side of the annulus, with the internal leaflets being enclosed and protected by the tubular ascending aorta. Chemical fixation may be accomplished using a variety of techniques and chemicals, though the most common procedure used involves supporting the tubular valve element on at least the ascending aorta or outflow portion with a fixation insert, immersing the assembly in a bath of fixing solution (e.g., glutaraldehyde), and either flowing fixing solution through the valve element or maintaining a predetermined pressure differential across the leaflets during the fixation process. See, for example, U.S. Pat. No. 4,372,743 to Lane, which describes maintaining a low pressure differential across the leaflets of between 1–4 mm Hg.

The use of fixation inserts is also quite effective in shaping the valve during the fixation process. For example, U.S. Pat. No. 5,197,979 to Quintero, et al. describes inserts having three outwardly convex regions for shaping the valve sinuses. More recently, U.S. Pat. No. 6,001,126 to Nguyen, et al. discloses inserts having a plurality of pin holes in the two convex regions corresponding to the coronary sinuses that enable coronary artery shaping plugs or mandrels to be mounted thereon. Whichever type of insert is used, the ultimate size of the fixed valve is influenced, at least in the sinus regions, by the insert. Preferably, the relative size of the annulus and sinus regions is identical to the human aortic valve being replaced. It is therefore very important to begin with a donor valve having an accurately sized annulus.

The fixation process causes some shrinkage in the tissue. Therefore, the sizing of fresh tissue provides only an estimate of the annulus size of the fixed tissue. The amount of shrinkage depends on the chemicals used, the duration of fixation, the pressure differentials within the valve, any heating that is applied, and other less significant factors. Because of these variables, fixed porcine aortic valves are sized once again using a caliper and/or a sizing stent to sort the valves into mounting sizes.

Another consideration for proper valve sizing is the dynamic expansion and contraction experienced in use after implantation. One study by Hansen, entitled Longitudinal and Radial Distensibility of the Porcine Aortic Root (Department of Electrical Engineering, the University of Western Ontario, London, Ontario, June 1994) showed that the aortic root might contract radially up to 25%, and longitudinally up to 12% when heart is arrested and the aortic root is under no pressure. The study suggests sizing the bioprosthetic replacement valve approximately 30% greater in diameter than the native aortic root at zero pressure to accommodate the expected expansion.

It is thus apparent that an accurate and reliable means for estimating, from the fresh valve, the annulus size of a fixed xenograft valve annulus is needed to increase valve yield and quality, and reduce expense.

SUMMARY OF THE INVENTION

The present invention provides an apparatus for sizing fresh donor heart valves that have a lumen and an inwardly-directed valve annulus within the lumen. The apparatus includes a sizing member having an axially-extending sizing portion with a forward end adapted to insert within the lumen of the donor heart valve. The sizing portion increases in size along an axis from the forward end such that a region on the exterior thereof eventually contacts the valve annulus upon continued insertion of the sizing portion within the lumen. A measuring bracket connects to the sizing member and has a scale portion spaced from and generally aligned with the sizing portion, the scale portion providing markings indicating the annulus size of the donor heart valve relative to the position of the donor heart valve on the sizing portion. In a preferred embodiment, the sizing portion is conical having a taper of between 1–6 degrees. The measuring bracket may include a mounting portion generally perpendicular to the scale portion and including a through hole into which the sizing portion fits in an interference.

In a further embodiment, the present invention provides a method of measuring the annulus of a fresh donor heart valve including the steps of obtaining a fresh donor heart valve, and providing a sizer having an axially-extending sizing portion adapted to fit within a lumen of the fresh donor heart valve. The sizing portion has an exterior surface that increases in size from a forward end along its axis to eventually contact an inwardly-directed valve annulus within the lumen of the fresh valve. The method includes inserting the forward end of the sizing portion into the donor heart valve lumen, and halting the insertion at a predetermined resistance to further insertion. After halting further insertion of the sizing portion into the lumen, the valve annulus size is determined based on the distance that the sizing portion has been inserted. In a preferred embodiment, the sizer further includes a measuring bracket connected thereto having a scale portion spaced from and generally aligned with the sizing portion. The valve size is determined by observing the position of the donor heart valve with respect to the scale portion of the measuring bracket.

In another aspect of the invention, a method of manufacturing prosthetic heart valves is provided. A supply a fresh donor heart valve isolations is provided at a slaughterhouse. The annulus size of the heart valve isolations is measured using a sizer having a sizing portion for insertion within the lumen of the isolation. The method includes selecting a subset of the supply based on the step of measuring, and shipping the subset from slaughterhouse to a valve manufacturing facility. Finally, at least one prosthetic heart valve is fabricated from a donor heart valve isolation selected from the subset.

The present invention also provides an apparatus for sizing a fresh donor heart valve, the fresh valve having a lumen and an inwardly-directed annulus. The apparatus includes a sizer having an axially-extending sizing portion with a forward end adapted to insert within the lumen, the sizing portion having a length of between about 5.08–15.24 cm (2–6 inches). The sizing portion may be conical, and desirably has a taper of between about 2–4 degrees. In one embodiment, the sizing portion is made of a lubricious material, preferably polytetrafluoroethylene. The sizer further may include a measuring bracket connected thereto having a scale portion spaced from and generally aligned with the sizing portion The scale portion provides markings indicating the annulus size of the donor heart valve relative to the position of the donor heart valve on the sizing portion. The markings are desirably supplemented with numerical indicators of valve size, either in terms of valve diameter in millimeters or as non-dimensional numbers in conjunction with a separate chart to correlate the numerical indicators with valve size. The markings may be calibrated for fresh valves from a particular geographic supply source.

DESCRIPTION OF THE PREFERRED EMBODIMENTS

The present invention provides a sizer for fresh xenograft valves, for instance porcine valves. As mentioned above, porcine valves are the most common type of intact xenograft valves assembled into bioprosthetic heart valves for implantation in the human body. However the sizer and method of the present invention are suitable for measuring any type of xenograft valves, or even homograft valves for that matter, so long as the valve has been isolated from the host heart. Therefore, it should be understood that the term "donor heart valve" pertains to any valve from a mammal that has been substantially isolated from the surrounding heart tissue, and which is suitable for assembly into a bioprosthetic heart valve. Of course, "donor" does not imply a voluntary donation in the context of non-human tissue sources.

Figure 1:
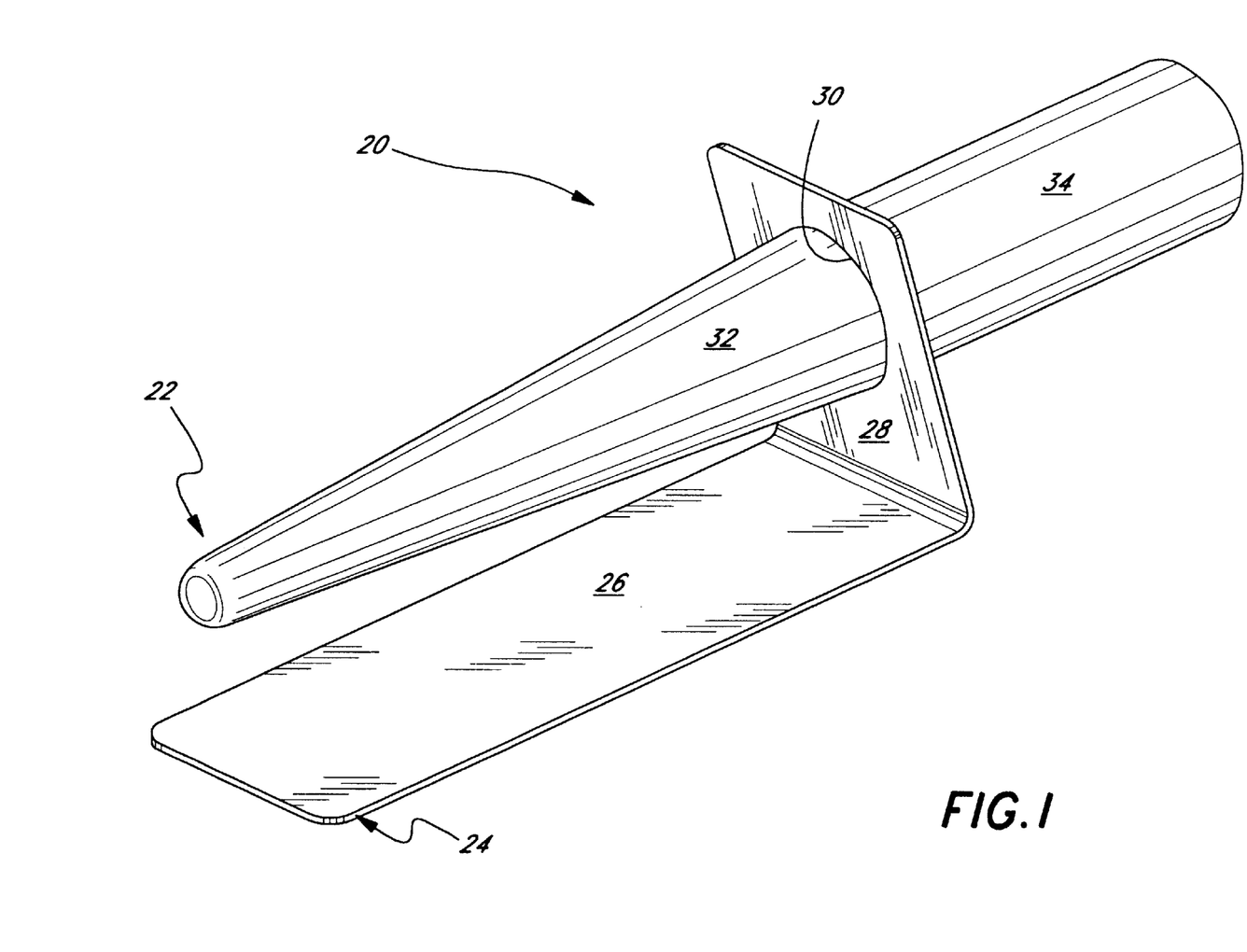
FIG. 1 is a perspective view of an exemplary fresh xenograft valve sizer of the present invention.
Figure 2:
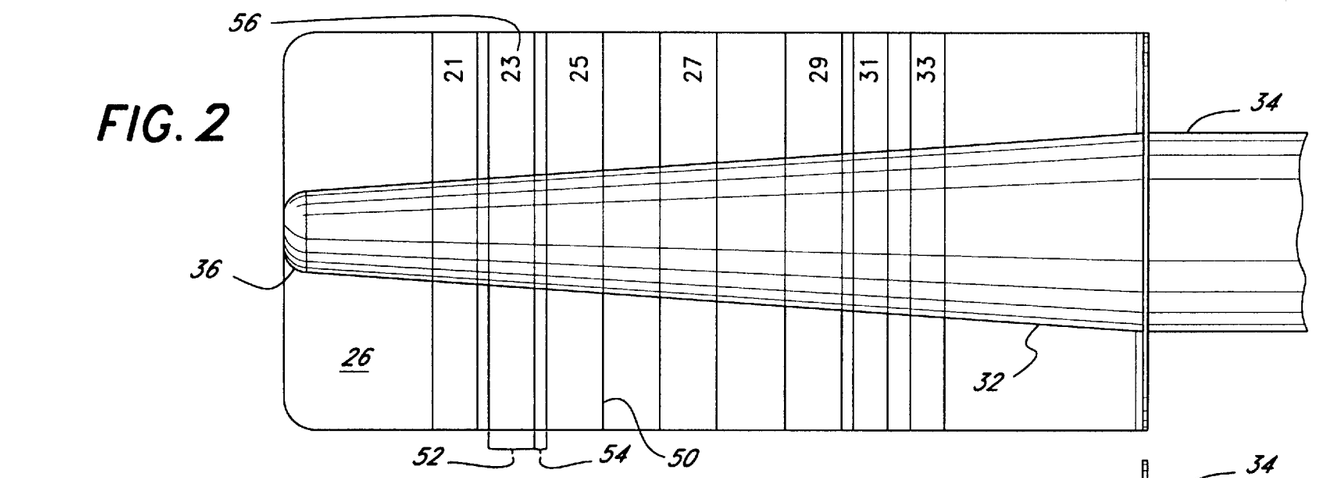
FIG. 2 is a top plan view of the sizer of FIG. 1.
Figure 3:
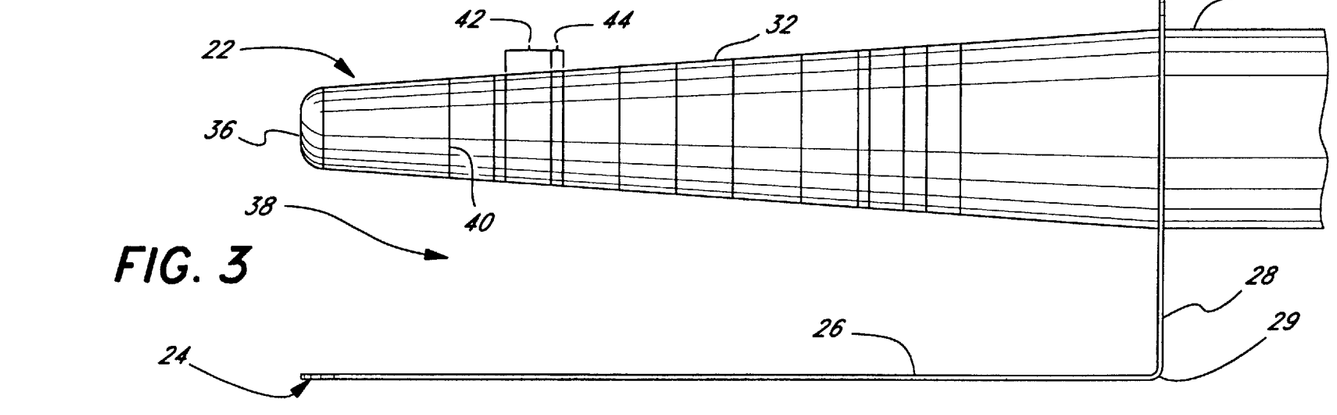
FIG. 3 is a side elevational view of the sizer of FIG. 1.

With reference to FIGS. 1–3, a valve sizer 20 of the present invention is shown comprising a sizer member 22 connected to a measuring bracket 24. The illustrated measuring bracket 24 comprises a scale portion 26 and a mounting portion 28 having a relatively large through hole 30. The measuring bracket 24 is desirably formed from a single elongated, flat sheet of rigid material, preferably stainless-steel, such that the scale portion 26 and mounting portion 28 are generally rectangular in shape and joined at a bend 29 (FIG. 3). The bend 29 is 90° to most efficiently accommodate the interaction between the sizer member 22 and measuring bracket 24, as will be explained below, although other bend angles are possible.

The sizer member 22 includes a generally conical sizing portion 32, and a handle portion 34 that may be cylindrical as shown or otherwise. A truncated forward end 36 of the conical sizing portion 32 defines rounded corners to facilitate insertion of the sizing portion into the inflow end of a donor valve. The sizer member 22 mounts to the measuring bracket 24 such that an elongated gap 38 (FIG. 3) is formed between the sizing portion 32 and the scale portion 26. This gap 38 accommodates portions of a generally tubular donor valve as it is inserted over the sizing portion 32. In the illustrated embodiment, the sizer member 22 mounts within the through hole 30 in the mounting portion 28 of the measuring bracket 24. Desirably, a simple interference fit holds the two elements together, with the hole 30 being sized slightly smaller than the maximum diameter of the conical sizing portion 32. Of course, many other configurations for mounting the sizing portion 32 across the gap 38 from the scale portion 26 may be utilized.

The sizer member 22 may be a formed a variety of generally rigid material, although polytetrafluoroethylene (PTFE or TEFLON) is preferred for its natural surface lubricity. As will be explained below, the sizing procedure involves inserting the sizing portion 32 into the inflow end of a donor valve until further advancement becomes more difficult. Of course, the difficulty of advancing the conical sizing portion 32 into a generally tubular tissue valve depends to an extent on the level of friction between the two surfaces. It should be understood, therefore, that the sizing portion 32 might be formed of material other than polytetrafluoroethylene, such as stainless-steel, for example, but that the different material may result a different insertion length for any one size of donor valve.

With reference now to FIGS. 2 and 3, the sizing portion 32 of the sizing member 22, and the scale portion 26 of the measuring bracket 24 both exhibit a series of corresponding linear markings thereon to indicate valve size. More specifically, the conical sizing portion 32 includes a plurality of circular markings 40 along its length and in planes perpendicular to the axis of the cone. The markings 40 may be inscribed in the surface of the sizing portion 32, or may be imprinted thereon with a suitable die, or both. The markings 40 are spaced apart along the axis of the sizing portion 32 to delineate regions of different valve sizes. For example, the region indicated at 42 is calibrated for a particular valve annulus size such that the sizing portion 32 may be inserted into the inflow end of a fresh valve having that annulus size, and the annulus will fit snugly over the sizing portion in the region 42. Of course, as the regions 42 move from the forward end 36 toward the handle 34, the corresponding valve size increases. The sizing portion 32 further includes at least one reject region 44 between two of the annulus size regions 42. Although the presence of the reject region 44 will be explained further below, it is sufficient at this stage for the reader to understand that any valve that is sized within this region will be rejected.

FIG. 2 illustrates a plurality of linear markings 50 on the scale portion 26 of the measuring bracket 24 that correspond to the markings 40 on the sizing portion 32. For example, an acceptable valve sizing region 52 defined within two of the markings 50 corresponds to the region 42 of sizing portion 32 shown in FIG. 3. Likewise, a reject region 54 on the scale portion 26 corresponds to the reject region 44 on the sizing portion 32. The markings 50 are also arranged perpendicular to the axis of the conical sizing portion 32, which happens to be perpendicular to the 90 degree bend 29 in the measuring bracket 24.

To identify the series of valve sizing regions 52 (which also serves to identify the valve sizing regions 42), a plurality of numerical indicia 56 are provided on the scale portion 26 of the measuring bracket 24. These numerical indicia 56 are positioned equidistantly between two of the markings 50 within each of the sizing regions 52, and identify that particular sizing region with a valve diameter size, in millimeters. The illustrated embodiment shows numerical indicia 56 from 19 to 33 millimeters. The reject regions 54 occupy the spaces between each two adjacent numbered regions 52, and have no numerical indicia.

Figure 4:
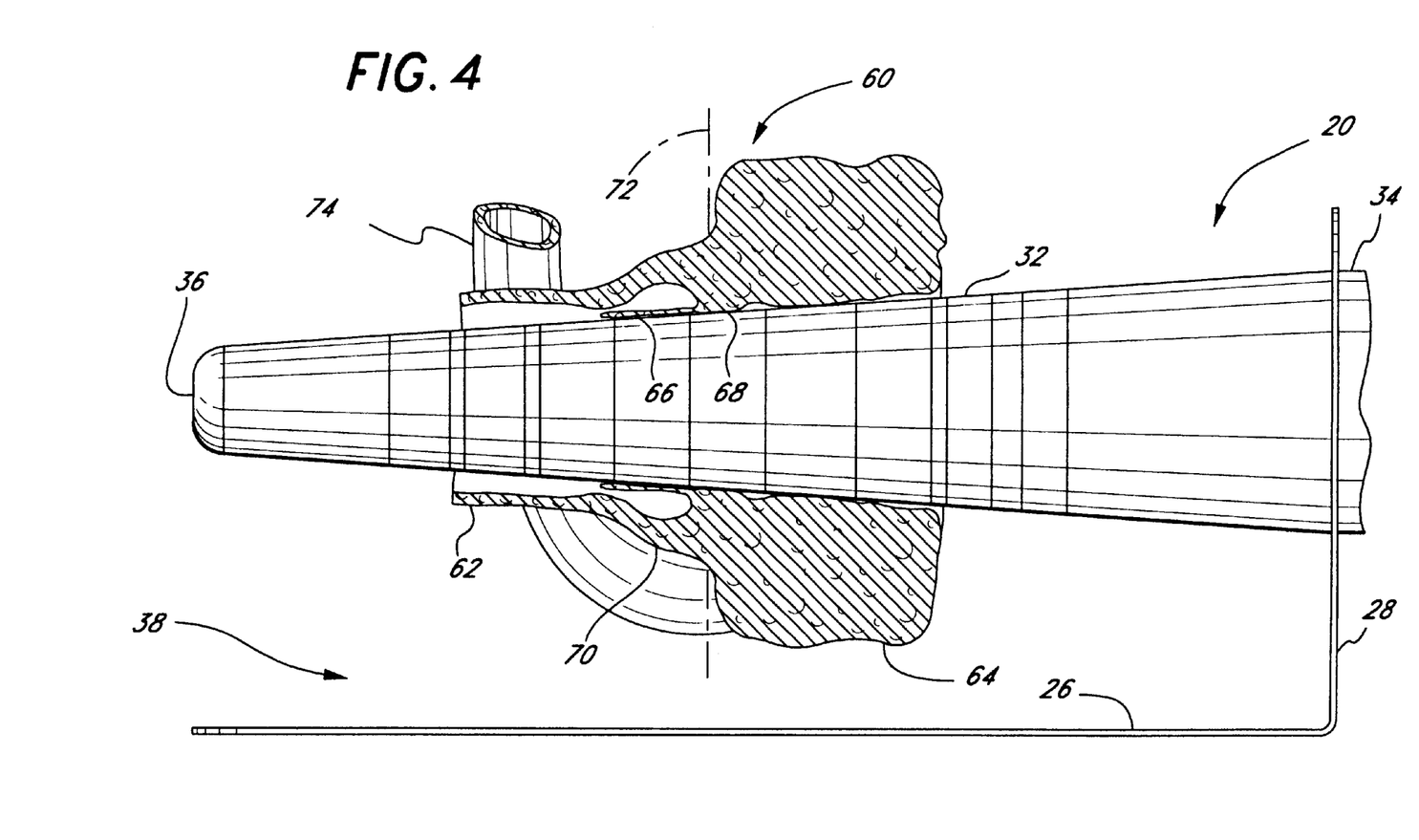
FIG. 4 is an elevational view of the sizer inserted into a porcine aortic valve isolation, shown in cross-section, and indicating a typical sizing method.

In use, as seen in FIG. 4, an aortic valve isolation 60, prepared as indicated above, is measured by inserting the sizing portion 32 of the valve sizer 20. Specifically, the forward end 36 of the sizing portion 32 inserts within the generally tubular inflow lumen of the valve isolation 60. The aortic valve isolation 60 comprises a tubular ascending aorta 62 on the outflow end, a generally thicker section of heart muscle tissue 64 of the inflow end, and a plurality of flexible leaflets 66 extending radially inward from an inner annulus 68 and angled generally toward the outflow end of the valve. As seen in FIG. 4, when the conical sizing portion 32 inserts within the lumen of the valve isolation 60, the leaflets 66 splay outward.

The aortic valve isolation 60 exhibits a plurality of outward bulges 70 indicating where the inner sinuses of the isolation 60 are located, namely in the area just downstream of the annulus 68. For purpose of this discussion, the exterior bulges 70 represent the sinuses, and thus will be referred to as the sinuses. As is well-known, the sinuses 70 induce a favorable blood flow profile that facilitates closing of the valve leaflets 66. In the aortic valve, there are three leaflets 66 and three sinuses. Coronary arteries (not shown) project outward from two of the sinuses, and are severed and ligated (tied off) prior to fixation. An imaginary reference line 72 is shown generally aligned with the aortic root that is between the annulus 68 and sinuses 70. The reference line 72 can be estimated from visual inspection of the exterior of the aortic valve isolation 60, as it generally corresponds to the base of the sinuses 70, where the muscle tissue 64 commences. The pulmonary artery 74 is also part of the aortic valve isolation 60 and is shown projecting from the adjacent tissue.

The conical sizing portion 32 inserts into the aortic valve isolation 60 until a predetermined resistance to further insertion is felt by the technician. The proper amount of resistance desirably correlates with the size markings 40 and 50 on the sizer 20. That is, the markings 40 and 50 are calibrated so as to reflect the correct valve size at a predetermined resistance to further insertion. As explained above, this resistance depends to some degree on the friction between the aortic valve isolation 60 and sizing portion 32. In a preferred embodiment, the sizing portion 32 is polytetrafluoroethylene, thus increasing the distance that the sizing portion 32 inserts into a particular aortic valve isolation 60 in comparison to a less lubricious material. In any event, the technician is trained to manually sense the proper resistance to further insertion, without further instrumentation. Of course, an apparatus for precisely measuring the resistance (e.g., in pounds) to further insertion of the sizing portion 32 may be utilized, if desired. Furthermore, other lubricious materials may be utilized with the resistance to further insertion of the sizing portion 32 through the aortic valve isolation 60 being altered accordingly. Still further, materials that are not considered to be naturally lubricious but which may be sterilized in an autoclave, such as stainless-steel or Delrin, may be suitable.

After the technician recognizes the proper resistance to further insertion of the sizing portion 32, he or she visually inspects the location of the sinuses 70, and in particular the imaginary reference line 72, so as to record the measured valve annulus size. That is, by observing the aortic valve isolation 60 with the scale portion 26 of the measuring bracket 24 in the background, the particular sizing region 52 with which the reference line 72 registers can be noted and recorded. If the reference line 72 registers with one of the reject regions 54, the aortic valve isolation 60 is rejected.

Subsequent to the sizing procedure of the present invention, the aortic valve isolation 60 is trimmed and then chemically fixed. The resulting tubular aortic valve is then further inspected for the proper size, and assembled into a prosthetic heart valve by adding components such as reinforcing fabric, stents, sewing rings, and the like.

With reference now to FIGS. 2 and 3, the spacing of the markings 40 and 50 on the sizing portion 32 and scale portion 26 respectively, will be described. One would expect the markings 40 and 50 to be equidistantly spaced because of the linear taper of the conical sizing portion 32. That is, the diameter of the sizing portion 32 increases linearly along its axis, and therefore one would expect that the measurement of the tubular body by the sizing portion would follow the same linear pattern. However, the present invention comprises increasing size markings 40 and 50 that follow a non-linear pattern.

For example, with reference to FIG. 2, the acceptable regions 52 on the scale portion 26 corresponding to 21, 23, and 25 mm valves, are generally linearly spaced apart. However, the width of each of these regions varies slightly. Moreover, a relatively large reject region 54 exists between the acceptable region 52 for the 25 mm measurement, and that for the 27 mm measurement. Likewise, an even larger reject region exists between 27 and 29 mm acceptable regions. Towards the larger size end of the scale, the reject regions 54 are reduced in size once again.

The particular spacing of the markings 40 and 50 has been determined by a statistical analysis of actual fresh valve measurements in conjunction with the final annulus size of valves prepared therefrom. A number of trends emerge from this analysis.

First of all, the reject regions 54 represent fresh valve sizes that do not regularly produce correctly sized final valves. That is, because of the 2 mm diameter increments between the annulus sizes of prepared valves, some fresh valves are sized such that they invariably fall into middle of two sizes when chemically fixed. That is, a particular fresh valve that is measured within the reject region 54 indicated in FIG. 2 almost never results in a final valve of close to 23 or 25 mm. Instead, the final valve size will be more like 24 mm, which is unacceptable.

A related trend is that the reject regions 54 are not all of the same width because fresh valves in the middle of the potential size range are less likely to fall within an acceptable size range in the finished valve in comparison to relatively smaller or larger fresh valves. That is, the reject regions 54 between the size regions 52 corresponding to the 25, 27, and 29 mm valves are larger than the other reject regions. This means that there is a larger range of actual fresh valve sizes that will be rejected within the middle of the potential size range.

A further trend is the varying widths of the acceptable size regions 52. For example, a relatively narrow width region 52 exists for 31 mm valves in comparison with the region for 29 mm valves.

It should be understood that the illustrated markings 40 and 50 are exemplary only, and may be modified based on a greater understanding of the correlation between fresh valve size and finished valve size for different geographical sources. The example shown was empirically derived from a number of statistical studies relying on sample sizes that are believed to be generally sufficient to obtain accurate correlation. However, further such studies may result in some refinement of the size scale shown.

Is also important to note that the particular taper of the conical sizing portion 32 directly affects the size scale, and has been carefully chosen to provide a balance between size resolution and accuracy in use. That is, the steeper the taper on the sizing region 32 the more defined will be the point at which the technician notices the aforementioned resistance to further insertion. Likewise, a shallower taper, especially when using polytetrafluoroethylene for the material of the sizing portion 32, will result in a less abrupt tactile feedback indicating the proper insertion resistance. Therefore, a minimum taper is required to enable the technician to identify the proper force resistance. However, the larger (i.e., steeper) the taper, the narrower will be the regions 52 and 54. Consequently, a maximum taper must be identified beyond which the resolution of the size scale becomes too small. Given these considerations, and when using polytetrafluoroethylene for the sizing portion 32, the taper (included angle of the cone) is desirably between 1–6°, preferably between 2–4°, and more preferably about 4°.

In terms of a specific embodiment, a preferred conical sizing portion 32 is based on an imaginary cone with a base radius of about 15.8 mm (0.62 inches) and a total axial length of about 22.6 cm (8.9 inches), corresponding to a taper angle of about four degrees. The region of the conical sizing portion 32 used to size fresh valves may be anywhere between 5.08–15.24 cm (2–6 inches), and more preferably between about 7.62–13.97 cm (3–5.5 inches). Therefore, the total length of the conical sizing portion 32 is desirably slightly greater than 5.08–15.24 cm (2–6 inches), and more preferably is about 15.24 cm (6 inches). This sizing length differentiates the present fresh valve sizer from sizers known in the art for measuring in-place valve annuluses. That is, sizers for measuring valve annuluses in a body are provided in sets, with one sizer per valve size. A set of valve sizers typically includes one each of 19–21–23–25–27–29–31–33 mm diameter sizers. Each of the sizers is therefore relatively short in axial length. Because the present sizer measures the size of donor valves in isolation, a conical sizing portion 32 having a relatively long length may be utilized.

The present invention greatly increases the yield of usable valves in a given sample from the slaughterhouse. The present sizer and aforementioned method of use are desirably implemented at the slaughterhouse, prior to shipping to the valve assembly facility. Because of the simple sizing procedure, very little training is required to effectively estimate the proper valve size. Therefore, if the valve assembly facility calls for a particular size of valve, which is typically the situation, then a number of valve isolations can be sized to sort out a subset of the particular size desired.

Figure 5:
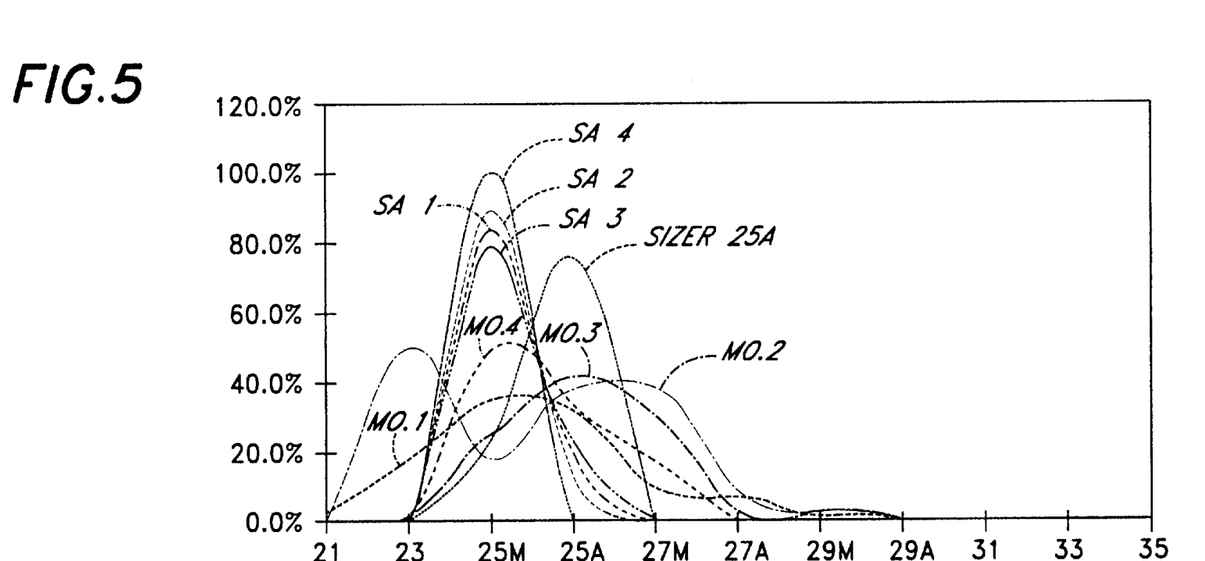
FIG. 5 is a graph showing the valve size distribution of a number of sample groups, both with and without the benefits of the present invention.
Figure 6:
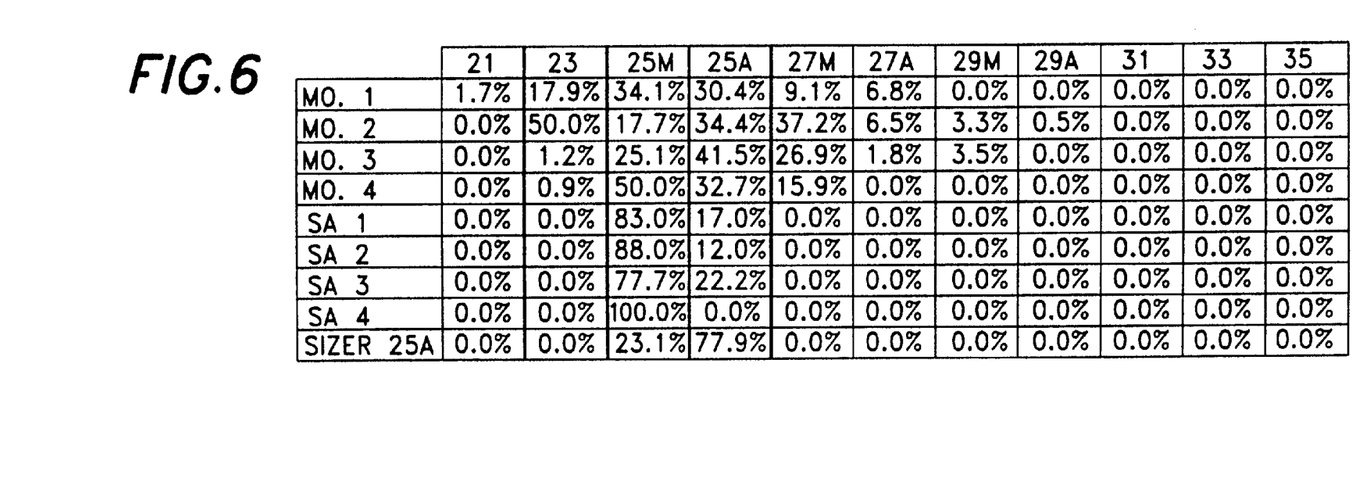
FIG. 6 is a table showing the discrete valve size distribution for the graph of FIG. 5.

Tests of the present sizer indicate that it is a relatively good predictor of valve size, and certainly better than the finger method previously employed. The graph of FIG. 5 and corresponding data table of FIG. 6 show valve size distributions for a number of batches of fresh porcine aortic valves. In each case, there was a request for fresh valves suitable for use in 25 mm finished valves.

The distributions range along the X-axis in terms of valve orifice diameters, in mm. There is a recognized manufacturing design size difference between the aortic and mitral positions for the same nominal orifice diameters. Accordingly, 25A (25 mm aortic) and 25M (25 mm mitral) sizes are shown, as well as for the 27 mm and 29 mm valves. The size distributions for four months (Mo. 1, Mo. 2, Mo. 3, and Mo. 4) of batches selected using the prior art method are relatively scattered between 21 and 27M sizes. With reference to the table of FIG. 6, the maximum percentage of fresh valves that were usable as 25M finished valves from any of the four months from using the prior art method was 50.5%, with the average for the four batches being substantially less.

In contrast, the four samples (SA1, SA2, SA3, and SA4) obtained using the sizer of the present invention produce a substantially higher percentage of usable valves. For instance, in one sample (SA4) 100% of the fresh valves were sized as estimated. By using the sizer of the present invention, the yield of usable valves from any one batch of fresh valves is substantially increased. This is a significant cost savings for the valve manufacturer. Moreover, because of the higher percentage of usable valves received, the quality control effort can focus on comparing valves that are quite similar in size so that only the best and most accurately sized valves are used, thus the quality of the finished valves is improved.

For additional confirmation of the efficacy of the present sizer and method, a sample of valves was measured trying to isolate a subset of 25A valves. The result indicated as SIZER 25A shows that nearly 79% of the valves inciated by the sizer of the present invention to be within the 25A size range were actually usable in that size valve.

Figure 7:
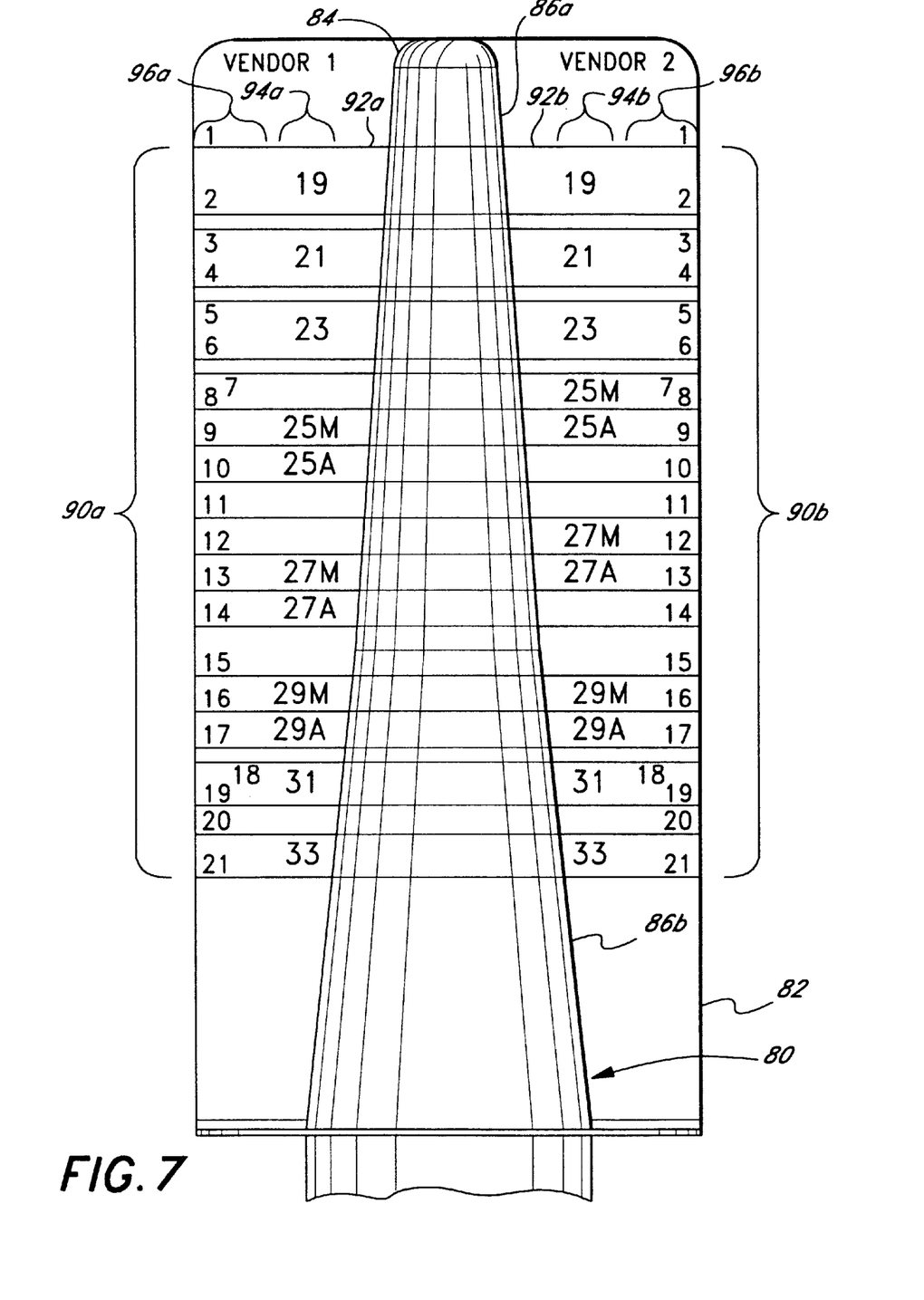
FIG. 7 is a top plan view of an alternative sizer of the present invention having two measurement scales and a dual-tapered sizing portion.

An alternative sizing portion 80 having regions with different tapers is seen in FIG. 7. The sizing portion 80 is shown against the backdrop of a measuring bracket 82, similar to those previously described. The sizer includes a rounded nose 84 at a leading end adjacent a first tapered section 86a that gradually widens along its axis until meeting a co-linear second tapered section 86b. The first tapered section 86a has a more shallow taper than the second tapered section 86b. In one embodiment, the first tapered section 86a has a taper angle as described above for the earlier embodiments, that is between 1–6°, and more preferably between 2–4°. The second tapered section 86b desirably has a taper angle slightly greater than the angle of the first tapered section 86a, and more preferably between 1–6° greater. In one specific embodiment, the first tapered section 86a has a taper angle of about 4°, while the second tapered section 86b has a taper angle of about 8°.

The measuring bracket 82 includes a first measurement scale 90a on the left side as seen in the drawing, and a second measurement scale 90b on the right side. As will be explained below, the first measurement scale 90a is calibrated for fresh valves received from a first vendor, and the second measurement scale 90b is calibrated for fresh valves received from a second vendor. The measuring bracket 82 includes a plurality of linear markings 92a, 92b corresponding to the first and second measurement scales 90a, 90b. For purpose of comparison of the two scales, the linear markings 92a on the left side coincide with the linear markings 92b on the right side, although this need not be the case. In either case, the linear markings 92a, 92b extend perpendicular to the axis of the sizing portion 80.

The linear markings 92a, 92b divide the respective measurement scales 90a, 90b into size regions, as described above. More specifically, each scale 90a, 90b includes a column of valve size indicators 94a, 94b (i.e., in mm corresponding to valve diameter), each of which is positioned between two of the linear markings 92a, 92b. As can be seen in FIG. 7, the valve size indicators 94a on the left side do not precisely line up with the valve size indicators 94b on the right side.

To further illustrate, and as an alternative means of measuring the fresh valve size, each of the measurement scales 90a, 90b includes a non-dimensional number column 96a, 96b (i.e., 1–21) corresponding to each of the linear markings 92a, 92b. As shown, the 23 mm size indicators 94a and 94b are both between the 5 and 6 in the respective number columns 96a, 96b, as are several other of the valve size indicators. However, the 25M (25 mm mitral) indicator in the left column 94a is between the 8 and 9 in the left number column 96a, while the 25M indicator in the right column 94b is between the 7 and 8 in the right number column 96b. In addition, several other of the valve size indicators do not line up between the first scale 90a and the second scale 90b.

The two scales 90a, 90b may be necessary if the fresh valves from different vendors have consistently different size characteristics. That is, valves from slaughterhouses in different geographical regions may have different characteristics because the donor animals, typically pigs, are genetically different, or have different feed. For example, pigs from the midwest of United States are typically corn fed, while those from the western United States may be fed with hay or other grasses. These and other differences may result in measurable variations in the conversion between fresh and fixed valve sizes. Indeed, as discussed above, the correlation between a particular fresh valve size and the final fixed valve size may be empirically determined. It has been found, therefore, that animals from different regions have different fresh-to-fixed valve size conversions. Therefore, as illustrated FIG. 7, different fresh valve size scales may be necessary for animals from different regions. Providing two scales 90a, 90b on one measurement bracket 82 permits one sizer to be used to measure valves from different vendors. Although this may be useful, any one valve sizer is typically used in the slaughterhouse, and thus measures valves from only one geographical source. Therefore, only one scale is necessary. The point being, however, that the scale is carefully calibrated for that particular geographical source.

One or both of the columns 94 or 96 may be used to identify the particular fresh valve size. For example, the valve size indicator column 94 calibrated for the particular geographical region may be used alone, as was seen in FIG. 2 above. Alternatively, if both the valve size indicator column 94 and the number column 96 are used the operator has a choice of which scale to compare the fresh valve. In a still further alternative, only the non-dimensional number column 96 may be provided, with a separate size correlation chart provided to the operator so that the particular valve size corresponding to each number range is known. Moreover, multiple size correlation charts for a single number column 96 may permit the same scale to be used to measure valves from different geographical regions. To facilitate this latter arrangement, multiple size correlation charts may be printed or scribed on the rear side of the measuring bracket 82 so the operator has a quick reference tool.

With reference to the alternative sizing portion 80 of FIG. 7, the transition between the first and second tapered sections 86a, 86b occurs in region of the measuring bracket 82 between the 14 and 15 in the number columns 96a, 96b. Therefore, the first tapered section 86a is used to measure valve sizes up to 27A (27 mm aortic), while the second tapered section 86b is used measure the larger valve sizes. This dual-tapered configuration may be desirable if the resistance to further insertion of the sizing portion 80 becomes increasingly further apart from valve size to valve size above 27A. That is, if the more shallow taper of the first tapered section 86a is used throughout, the sizing portion 80 may have to be excessively long to cover the full range of valve sizes. As a result, the second tapered section 86b is more steeply tapered, so that the entire range of valve sizes can be grouped together in a shorter axial distance.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. An apparatus for sizing fresh donor heart valves, the donor heart valves having a lumen and an inwardly-directed valve annulus within the lumen, the apparatus comprising:
    a sizing member having an axially-extending sizing portion with a forward end adapted to be inserted within the lumen, the sizing portion increasing in size along its axis from the forward end such that a region on the exterior thereof eventually contacts the valve annulus upon continued insertion of the sizing portion within the lumen; and
    a measuring bracket connected to the sizing member and having a scale portion spaced from and generally aligned with the sizing portion, the scale portion providing markings indicating the annulus size of the donor heart valve relative to the position of the donor heart valve on the sizing portion of the sizing member.

2. The apparatus of claim 1, wherein the sizing portion of the sizing member is conical and tapers down to the forward end.

3. The apparatus of claim 2, wherein the included angle of the taper is between about 1 and 6°.

4. The apparatus of claim 2, wherein the conical sizing portion includes a first section adjacent the forward end having a first taper angle, and a second section having a second taper angle larger than the first.

5. The apparatus of claim 1, wherein the sizing portion is made of a naturally lubricious material.

6. The apparatus of claim 5, wherein an included angle of the taper is between about 2–4°.

7. The apparatus of claim 1, wherein the measuring bracket comprises the scale portion extending in parallel to the axis of the siring portion, and a mounting portion extending generally perpendicular to the scale portion to which the sizing portion attaches.

8. The apparatus of claim 7, wherein the mounting portion includes a through hole, and wherein the sizing member mounts to the measuring bracket by an interference fit with the through hole.

9. The apparatus of claim 8, wherein the sizing member further includes a handle portion extending from the sizing portion through the through hole of the mounting portion of the measuring bracket in a direction opposite to the sizing portion.

10. The apparatus of claim 1, wherein the markings on the scale portion define regions indicating acceptable annulus size ranges.

11. The apparatus of claim 10, wherein at least one of the acceptable annulus size regions has a width that is different than at least one other acceptable annulus size region.

12. The apparatus of claim 10, wherein the markings on the scale portion further define regions indicating unacceptable annulus size ranges, the unacceptable annulus size regions being interposed between the acceptable annulus size regions.

13. A method of measuring the annulus size of a fresh donor heart valve, comprising:
    obtaining a fresh donor heart valve having a lumen and an inwardly-directed valve annulus within the lumen;
    providing a sizer having an axially-extending sizing portion adapted to fit within the lumen with an exterior surface that increases in size from a forward end along its axis;
    inserting the forward end of the sizing portion into the lumen of the donor heart valve;
    halting insertion of the sizing portion into tho lumen of the donor heart valve at a predetermined resistance to further insertion; and
    determining the valve annulus size based on the distance that the sizing portion is inserted into the lumen.

14. The method of claim 13, wherein the sizing portion is conical.

15. The method of claim 13, wherein the sizing portion is made of a naturally lubricious material.

16. The method of claim 13, the sizer further including a measuring bracket connected thereto having a scale portion spaced from and generally aligned with the sizing portion, wherein the step of determining includes observing the position of the donor heart valve with respect to the scale portion of the measuring bracket.

17. The method of claim 16, wherein the scale portion provides markings indicating the annulus size of the donor heart valve relative to the position of the donor heart valve on the sizing portion of the sizing member.

18. The method of claim 17, wherein the markings on the scale portion define regions indicating acceptable annulus size ranges.

19. The method of claim 18, wherein at least one of the acceptable annulus size regions has a width that is different than at least one other acceptable annulus size region.

20. The method of claim 18, wherein the step of observing comprises determining which annulus size region lines up with an anatomical feature on the exterior of the donor heart valve.

21. The method of claim 20, wherein the markings on the scale portion further define regions indicating unacceptable annulus size ranges, the unacceptable annulus size regions being interposed between the acceptable annulus size regions, and the method further includes discarding the donor heart valve if the anatomical feature registers with one of the unacceptable annulus size regions.

22. The method of claim 20, wherein the anatomical feature comprises a sinus region of the valve.

23. A method of manufacturing prosthetic heart valves, comprising:
    providing a supply of fresh donor heart valve isolations at a slaughterhouse;
    measuring the annulus size of the fresh donor heart valve isolations using a sizer having a sizing portion for insertion within the lumen of the donor heart valve isolations, the sizer being configured to identify the size of more than two sizes of the donor heart valve isolations;
    selecting a subset of the supply based on the step of measuring;
    shipping the subset of the supply from the slaughterhouse to a valve manufacturing facility; and fabricating at least one prosthetic heart valve from a donor heart valve isolation selected from the subset.

24. The method of claim 23, wherein the sizing portion is axially-extending and the sizer includes an axially-extending measuring scale spaced from and generally aligned with the sizing portion and formed on a measuring bracket including a mounting portion attached to the sizer.

25. The method of claim 24, wherein the step of me includes inserting the sizing portion into the lumen of the donor heart valve isolations until a predetermined resistance to further insertion is encountered, and visually observing an anatomical feature on the exterior of the heart valve isolations relative to the measuring scale.

26. The method of claim 25, wherein the anatomical feature is a valve sinus.

27. The method of claim 25, wherein the measuring scale includes regions indicating acceptable annulus size ranges, and the step of selecting includes selecting only those valves for which the anatomical feature falls within a predetermined acceptable annulus size range.

28. The method of claim 27, wherein the measuring scale further includes regions indicating unacceptable annulus size ranges, the unacceptable annulus size regions being interposed between the acceptable annulus size regions and the step of selecting includes rejecting those valves for which the anatomical feature falls within any unacceptable annulus size range.

29. An apparatus for sizing a fresh donor heart valve, the donor heart valve having a lumen and an inwardly-directed valve annulus within the lumen, the apparatus comprising:
   a sizer having an axially-extending sizing portion that includes a conical taper with a forward end adapted to be inserted within the lumen, the sizing portion having a length of between about 5.08–15.24 cm (2–6 inches).

30. The apparatus of claim 29, wherein the taper has an angle of between about 2–4 degrees.

31. The apparatus of claim 29, wherein the conical sizing portion includes a first section adjacent the forward end having a first taper angle, and a second section having a second taper angle larger than the first.

32. The apparatus of claim 31, wherein the fist and second taper angles are between 1–6°.

33. An apparatus for sizing a fresh donor heart valve, the donor heart valve having a lumen and an inwardly-directed valve annulus within the lumen, the apparatus comprising:
   a sizer having an axially-extending sizing portion with a forward end adapted to be inserted within the lumen, the sizing portion having a length of between about 5.08–15.24 cm (2–6 inches), where the sizer farther includes a measuring bracket connected thereto and having a scale portion spaced from and generally aligned with the sizing portion, the scale portion providing markings indicating the annulus size of the donor heart valve relative to the position of the donor heart valve on the sizing portion.

34. The apparatus of claim 33, where the markings are supplemented with numerical indicators of valve size.

35. The apparatus of claim 34, where the numerical indicators are in term of valve diameter in millimeters.

36. The apparatus of claim 34, where the numerical indicators are non-dimensional, and a separate scale to correlate the numerical indicators with valve size is provided.

37. The apparatus of claim 33, where the markings are calibrated for flesh valves from a particular geographic supply source.

* * * * *

UNITED STATES PATENT AND TRADEMARK OFFICE
CERTIFICATE OF CORRECTION

PATENT NO.    : 6,458,155 B1                                             Page 1 of 1
DATED         : October 1, 2002
INVENTOR(S)   : Son Van Nguyen, Hung Lam and Cuong Ton-That It is certified that error appears in the above-identified patent and that said Letters Patent is hereby corrected as shown below:

Column 11,
Line 50, after "of the" please delete "siring" and insert -- sizing --.

Column 12,
Line 16, after "into" please delete "tho" and insert -- the --.

Column 13,
Line 8, after "step of" please delete "me" and insert -- measuring --.

Column 14,
Line 7, after "wherein the" please delete "fist" and insert -- first --.
Line 15, after "sizer" please delete "farther" and insert -- further --.
Line 25, after "are in" please delete "term" and insert -- terms --.
Line 31, after "for" please delete "flesh" and insert -- fresh --.

Signed and Sealed this

Fourth Day of March, 2003

JAMES E. ROGAN
*Director of the United States Patent and Trademark Office*